US009307693B2

(12) United States Patent
Boday et al.

(10) Patent No.: US 9,307,693 B2
(45) Date of Patent: Apr. 12, 2016

(54) MICROCAPSULES ADAPTED TO RUPTURE IN A MAGNETIC FIELD

(71) Applicant: International Business Machines Corporation, Armonk, NY (US)

(72) Inventors: Dylan J. Boday, Tucson, AZ (US); Joseph Kuczynski, North Port, FL (US); Robert E. Meyer, III, Rochester, MN (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 14/245,074

(22) Filed: Apr. 4, 2014

(65) Prior Publication Data

US 2014/0215905 A1 Aug. 7, 2014

Related U.S. Application Data

(62) Division of application No. 13/283,734, filed on Oct. 28, 2011, now Pat. No. 8,741,804.

(51) Int. Cl.
*A01C 21/00* (2006.01)
*A01N 25/28* (2006.01)
(Continued)

(52) U.S. Cl.
CPC .............. *A01C 21/00* (2013.01); *A01N 25/00* (2013.01); *A01N 25/28* (2013.01); *C05G 3/0017* (2013.01); *C05G 3/0035* (2013.01)

(58) Field of Classification Search
None
See application file for complete search history.

(56) References Cited

U.S. PATENT DOCUMENTS 3,686,930 A    8/1972    Kniebes et al.
3,748,827 A    7/1973    Bulian et al.
(Continued)

FOREIGN PATENT DOCUMENTS

DE    19857697 A1    6/2000
DE    102005056052 A1    5/2007
(Continued)

OTHER PUBLICATIONS

Hu et al. "Controlled Rupture of Magnetic Polyelectrolyte Microcapsules for Drug Delivery", Langmuir 2008, 24, 11811-11818.*

(Continued)

*Primary Examiner* — Carlos Azpuru
*Assistant Examiner* — Casey Hagopian
(74) *Attorney, Agent, or Firm* — Matthew J. Bussan

(57) ABSTRACT

Controlled release of one or more agricultural chemicals is provided by microcapsules adapted to rupture in a magnetic field. The microcapsules, which may be applied to soil, seeds and/or plants, each have a shell that encapsulates an agricultural chemical, such as a fertilizer, herbicide or insecticide. One or more organosilane-coated magnetic nanoparticles is/are covalently bound into the shell of each microcapsule. For example, (3-aminopropyl) trimethylsilane-coated magnetite nanoparticles may be incorporated into the shell of a urea-formaldehyde (UF) microcapsule during in situ polymerization. In one embodiment, microcapsules encapsulating a fertilizer are applied during seed planting. Controlled release is subsequently triggered after an appropriate period of dormancy by positioning a magnetic field generating device proximate the microcapsules to generate a magnetic field sufficient to rupture the microcapsule shells through magnetic stimulation of the organosilane-coated magnetic nanoparticles. The ruptured microcapsule shells release the fertilizer.

3 Claims, 9 Drawing Sheets

(51) Int. Cl.
*A01N 25/00* (2006.01)
*C05G 3/00* (2006.01)

(56) References Cited

U.S. PATENT DOCUMENTS

| | | |
|---|---|---|
| 3,936,976 A | 2/1976 | Porter et al. |
| 3,956,179 A | 5/1976 | Sebestian et al. |
| 4,115,081 A | 9/1978 | Ohno et al. |
| 4,425,117 A | 1/1984 | Hugemann et al. |
| 4,657,843 A | 4/1987 | Fukuyama et al. |
| 4,670,299 A | 6/1987 | Fukuyama et al. |
| 4,781,733 A | 11/1988 | Babcock et al. |
| 4,904,632 A | 2/1990 | Pesek et al. |
| 4,950,314 A | 8/1990 | Yamada et al. |
| 4,965,062 A | 10/1990 | Van Dijk et al. |
| 5,147,957 A | 9/1992 | Kumar |
| 5,233,071 A | 8/1993 | Wilczek |
| 5,286,280 A | 2/1994 | Chiou |
| 5,733,663 A | 3/1998 | Scheunemann et al. |
| 5,741,579 A | 4/1998 | Nishizawa |
| 5,777,007 A | 7/1998 | Kagawa et al. |
| 5,876,739 A | 3/1999 | Turnblad et al. |
| 5,925,595 A | 7/1999 | Seitz et al. |
| 6,001,943 A | 12/1999 | Enami et al. |
| 6,060,530 A | 5/2000 | Chaouk et al. |
| 6,165,253 A | 12/2000 | Sirkar et al. |
| 6,339,166 B1 | 1/2002 | Allcock et al. |
| 6,417,236 B1 | 7/2002 | Hobson et al. |
| 6,514,439 B2 | 2/2003 | Van Koppenhagen et al. |
| 6,673,246 B2 | 1/2004 | Markowitz et al. |
| 6,682,751 B1 | 1/2004 | Hargrove et al. |
| 6,710,181 B2 | 3/2004 | Kumagai et al. |
| 6,805,964 B2 | 10/2004 | Clouser et al. |
| 6,858,634 B2 | 2/2005 | Asrar et al. |
| 6,900,269 B2 | 5/2005 | Hwang et al. |
| 6,972,249 B2 | 12/2005 | Akram et al. |
| 6,986,943 B1 | 1/2006 | Cook et al. |
| 7,056,522 B2 | 6/2006 | Voris et al. |
| 7,101,394 B2 | 9/2006 | Hamm et al. |
| 7,169,832 B2 | 1/2007 | Poppe et al. |
| 7,211,192 B2 | 5/2007 | Shea et al. |
| 7,553,901 B2 | 6/2009 | Horikoshi et al. |
| 7,585,320 B2 | 9/2009 | Hamm et al. |
| 7,687,722 B2 | 3/2010 | Japp et al. |
| 7,759,406 B2 | 7/2010 | Kumon et al. |
| 7,767,219 B2 | 8/2010 | Weber et al. |
| 7,767,736 B2 | 8/2010 | Baran, Jr. |
| 7,814,737 B2 | 10/2010 | Pierson |
| 7,851,055 B2 | 12/2010 | Fukushima |
| 2002/0014154 A1 | 2/2002 | Witzko et al. |
| 2002/0119317 A1 | 8/2002 | Gan et al. |
| 2003/0022791 A1* | 1/2003 | Asrar et al. ............... 504/116.1 |
| 2003/0173255 A1 | 9/2003 | White et al. |
| 2004/0149127 A1 | 8/2004 | Lyons et al. |
| 2006/0000766 A1 | 1/2006 | Ji |
| 2006/0118490 A1 | 6/2006 | Landry et al. |
| 2007/0023957 A1 | 2/2007 | Kotov et al. |
| 2007/0164271 A1 | 7/2007 | Wait, Jr. |
| 2007/0241303 A1 | 10/2007 | Zhong et al. |
| 2007/0251393 A1 | 11/2007 | Pope et al. |
| 2007/0257091 A1 | 11/2007 | Kuczynski |
| 2007/0270536 A1 | 11/2007 | Sachdev et al. |
| 2008/0097014 A1 | 4/2008 | Park et al. |
| 2008/0191729 A1 | 8/2008 | Blanco et al. |
| 2008/0193543 A1* | 8/2008 | Morello et al. ............... 424/490 |
| 2008/0210087 A1 | 9/2008 | Ku et al. |
| 2008/0264563 A1 | 10/2008 | Kuczynski et al. |
| 2009/0004488 A1 | 1/2009 | Park et al. |
| 2009/0117373 A1 | 5/2009 | Wisniewski et al. |
| 2009/0142638 A1 | 6/2009 | Katayama |
| 2010/0027192 A1 | 2/2010 | Perry et al. |
| 2010/0030185 A1 | 2/2010 | Hood et al. |
| 2010/0234481 A1 | 9/2010 | Sugimoto et al. |
| 2010/0240811 A1 | 9/2010 | He et al. |
| 2010/0243520 A1 | 9/2010 | Glover et al. |
| 2011/0092640 A1 | 4/2011 | Tzou |
| 2011/0097416 A1 | 4/2011 | Nguyen et al. |
| 2011/0189381 A1 | 8/2011 | Boday et al. |
| 2012/0187046 A1 | 7/2012 | Boday et al. |
| 2012/0256224 A1 | 10/2012 | Hatanaka et al. |
| 2012/0279768 A1 | 11/2012 | Boday et al. |
| 2013/0034739 A1 | 2/2013 | Boday et al. |
| 2013/0131244 A1 | 5/2013 | Dickens |

FOREIGN PATENT DOCUMENTS

| | | |
|---|---|---|
| EP | 0315836 A2 | 5/1989 |
| JP | 53-42181 A | 4/1978 |
| JP | 61144339 A | 7/1986 |
| JP | 2000-297094 | 10/2000 |
| JP | 2005197609 A | 7/2005 |
| WO | 2006/096033 A1 | 9/2006 |
| WO | 2011078010 A1 | 6/2011 |

OTHER PUBLICATIONS

Yamaura et al. "Preparation and characterization of (3-aminopropyl) triethoxysilane-coated magnetite nanoparticles", Journal of Magnetism and Magnetic Materials 279 (2004) 210-217.*
CAS Registry No. 2530-83-8, SciFinder, American Chemical Society (ACS), 2015, 1 page.
U.S. Appl. No. 14/512,491, to Boday et al., entitled "Flame Retardant Filler", filed Oct. 13, 2014, assigned to International Business Machines Corporation.
U.S. Appl. No. 13/204,009 to Boday et al., entitled "Microcapsules adapted to Rupture in a Magnetic Field to Enable Easy Removal of One Substrate from Another for Enhanced Reworkability," filed Aug. 5, 2011.
Shang-Hsiu Hu et al., "Controlled Rupture of Magnetic Polyelectrolyte Microcapsules for Drug Delivery," Langmuir, vol. 24, No. 20, pp. 11811-11818, 2008.
B. J. Blaiszik et al., "Microcapsules filled with reactive solutions for self-healing materials," Polymer, vol. 50, pp. 990-997, 2009.
E. N. Brown et al., "In situ poly(urea-formaldehyde) microencapsulation of dicyclopentadiene," Journal of Microencapsulation, vol. 20, No. 6, pp. 719-730, 2003.
M. Yamaura et al., "Preparation and characterization of (3-aminopropyl) triethoxysilane-coated magnetite nanoparticles," Journal of Magnetism and Magnetic Materials, vol. 279, pp. 210-217, 2004.
S. F. Peteu et al., "Responsive Polymers for Crop Protection," Polymers, vol. 2, pp. 229-251, Aug. 19, 2010.
J. Liu et al., "Magnetically Sensitive Alginate-Templated Polyelectrolyte Multilayer Microcapsules for Controlled Release of Doxorubicin," Journal of Physical Chemistry C, vol. 114, No. 17, pp. 7673-7679, Apr. 14, 2010.
M. Alley et al., "Pop-up and/or Starter Fertilizers for Corn," Virginia Cooperative Extension Publication 3002-1438, pp. 1-5, 2010.
Guoliang Zhang, E.L. Cussler, "Hollow fibers as structured distillation packing", Journal of Membrane Science, vol. 215, Issues 1-2, Apr. 15, 2003, pp. 185-193.
J. Andrieu, "Influence of Wettability on Liquid Phase Texture in a Countercurrently Irrigated Packing", Chemical Engineering Science, vol. 30, 1975, pp. 217-220.
Barry S. Hindin, "Silver Sulfide Corrosion Control Using Corrosion Prevention Compounds", Corrosion 2006, Mar. 12-16, 2006, San Diego, California, Paper No. 06264, Copyright 2006, NACE International.
English translation of DE 19857697 A1, Jun. 15, 2000.
U.S. Appl. No. 12/696,328, to Boday et al., entitled "Anti-Corrosion Conformal Coating for Metal Conductors Electrically Connecting an Electronic Circuit", filed Jan. 29, 2010, assigned to International Business Machines Corporation.
Wikipedia contributors, "Natural gas processing", Wikipedia, The Free Encyclopedia, http://en.wikipedia.org/w/index.php?title=Natural_gas_processing&oldid=400027904 (accessed Dec. 13, 2010).

(56) References Cited

OTHER PUBLICATIONS

Wikipedia contributors, "Silsesquioxane", Wikipedia, The Free Encyclopedia, http://en.wikipedia.org/w/index.php?title=Silsesquioxane&oldid=402217379 (accessed Dec. 13, 2010).
"UCARSOL GT 10 Antifoam", Product Information, Gas Treating Products & Services, The Dow Chemical Company, Midland, Michigan, Published Jul. 2004. (Available at http://www.dow.com/gastreating/solution/ngp_osr.htm).
"Hydrogen Sulfide Removal Methods", Excel Water Technologies, Inc., Fort Lauderdale, Florida, dated 2007. (Available at http://www.excelwater.com/eng/b2c/h2s.php).
I. Manconi et al., "Removal of H2S and Voltatile Organic Sulfur Compounds by Silicone Membrane Extraction", Research Article, Society of Chemical Industry, Aug. 4, 2008, pp. 69-77.
U.S. Appl. No. 13/010,995, to Boday et al., entitled "Silicone-Based Chemical Filter and Silicone-Based Chemical Filter and Silicone-Based Chemical Bath for Removing Sulfur Contaminants", filed Jan. 21, 2011, assigned to International Business Machines Corporation.
U.S. Appl. No. 13/802,543, to Boday et al., entitled "Silicone-Based Chemical Filter and Silicone-Based Chemical Bath for Removing Sulfur Contaminants", filed Mar. 13, 2013, assigned to International Business Machines Corporation.
U.S. Appl. No. 13/802,652, to Boday et al., entitled "Silicone-Based Chemical Filter and Silicone-Based Chemical Bath for Removing Sulfur Contaminants", filed Mar. 13, 2013, assigned to International Business Machines Corporation.
Kumar et al., "Instantaneous, Facile and Selective Synthesis of Tetrabromobisphenol A using Potassium Tribromide: An Efficient and Renewable Brominating Agent", Organic Process Research & Development, vol. 14, No. 1, 2010, pp. 174-179, Published on Web Dec. 20, 2009.
U.S. Appl. No. 13/102,306, to Brody et al., entitled "Flame Retardant Filler", filed May 6, 2011, assigned to International Business Machines Corporation.
"Flame Retardant Fact Sheet; Other Phosphorous Flame Retardants", European Flame Retardants Association, Sep. 28, 2011, 2 pages. (http://www.cefic-efra.com/images/stories/factsheet/7OtherPhosphorousFactSheetAB-1_00.pdf).
U.S. Appl. No. 13/397,010, to Boday et al., entitled "Non-Halogenated Flame Retardant Filler", filed Feb. 15, 2012, assigned to International Business Machines Corporation.
Dean et al., "Characterization of a Thermal Interface Material for Burn-in Application", 2000, 6 pages. <https://www51.honeywell.com/sm/em/common/documents/4.2_technical_papers_2000_4.pdf>.
"Development of Heat-dissipating Sheets achieving both Metal-like High Thermal Conductivity and Flexibility", News Release, Hitachi Chemical Co., Ltd., Japan, Jun. 23, 2009, 3 pages. <http://www.hitachi-chem.co.jp/english/information/2009/n_090623.html>.
"Hi-Flow 225FT; Reworkable, Pressure Sensitive Phase Change Material", Product Brochure, The Bergquist Company, Chanhassen, Minnesota, 2008, 1 page. <http://www.bergquistcompany.com/pdfs/dataSheets/PDS_HF_225FT_12.08_E.pdf>.
U.S. Appl. No. 13/495,132, to Boday et al., entitled "Thermal Interface Material (TIM) With Thermally Conductive Integrated Release Layer", filed Jun. 13, 2012, assigned to International Business Machines Corporation.
Christopher O. Muller, "Control of Corrosive Gases to Avoid Electrical Equipment Failure", Purafil, Inc., webpage: www.purafil.com/literature/control-of-corrosive-gases.pdf, 1999, pp. 1-13.
Manuel A. Rivera, "Design Considerations for Reliable Electrical, Control and Instrumentation Systems in Geothermal Power Plants With Emphasis on Hydrogen Sulphide Related Problems", Geothermal Training Programme; United Nations University; 2007, pp. 461-490.
Ezdine Ferjani et al., "Bulk and surface modification of cellulose diacetate based RO/NF membranes by polymethylhydrosiloxane—Preparation and characterization", Desalination, vol. 146, Issues 1-3, 2002, pp. 325-330.
Ronald L. Cicero et al., "Photoreactivity of Unsaturated Compounds with Hydrogen-Terminated Silicon (111)", Langmuir, vol. 16, Issue 13, 2000, pp. 5688-5695.
John H. MacMillan, Ph.D., "Homogeneous Platinum Catalysts", United Chemical Technologies, Inc., 2008, 69 pages.
Rosaria Ciriminna, et al., "Closing the Organosilicon Synthetic Cycle: Efficient Heterogeneous Hydrosilylation of Alkenes over SiliaCat Pt(0)", ACS Sustainable Chemistry & Engineering, 2012, 5 pages.
U.S. Appl. No. 13/283,734, to Boday et al., "Microcapsules Adapted to Rupture in a Magnetic Field", filed Oct. 28, 2011, assigned to International Business Machines Corporation.
U.S. Appl. No. 14/930,336, to Boday et al., entitled "Microcapsules Adapted to Rupture in a Magnetic Field to Enable Easy Removal of One Substrate from Another for Enhanced Reworkability", filed Nov. 2, 2015, assigned to International Business Machines Corporation.
King, David L., et al., "Removal of Sulfur Components from Low Sulfur Gasoline Using Copper Exchanged Zeolite Y at Ambient Temperature", Pacific Northwest Laboratory, Richland, Washington, 2005, 1 page. (Available at http://iic.pnl.gov/abstracts/nacsp/p_001.pdf).
English Language Translation of Claims in CN101033327 (2007), 2 pages.
U.S. Appl. No. 14/244,921, to Boday et al., entitled "Microcapsules Adapted to Rupture in a Magnetic Field", filed Apr. 4, 2014, assigned to International Business Machines Corporation.
U.S. Appl. No. 14/244,964, to Boday et al., entitled "Microcapsules Adapted to Rupture in a Magnetic Field", filed Apr. 4, 2014, assigned to International Business Machines Corporation.
English language machine translation of abstract of JP53-42181 (1978), 1 page.
U.S. Appl. No. 15/015,905, to Boday et al., entitled "Flame Retardant Filler", filed Feb. 4, 2016, assigned to International Business Machines Corporation.
U.S. Appl. No. 15/044,150, to Boday et al., entitled "Removing Sulfur Contaminants From Water Using a Silicone-Based Chemical Filter", filed Feb. 16, 2016, assigned to International Business Machines Corporation.
U.S. Appl. No. 15/044,175, to Boday et al., entitled "Removing Sulfur Contaminants From a Fluid Using a Silicone-Based Chemical Filter", filed Feb. 16, 2016, assigned to International Business Machines Corporation.

* cited by examiner

700

```
┌─────────────────────────────────────────────────┐
│         PROVIDE MICROCAPSULES ADAPTED TO         │
│  RUPTURE IN A MAGNETIC FIELD FOR CONTORLLED     │─ 705
│  RELEASE OF ONE OR MORE AGRICULTURAL CHEMICALS  │
│                    (FIG. 6)                      │
└─────────────────────────────────────────────────┘
                         │
                         ▼
┌─────────────────────────────────────────────────┐
│        COAT SEED WITH THE MICROCAPSULES          │─ 710
└─────────────────────────────────────────────────┘
```

POSITION A MAGNETIC FIELD GENERATING DEVICE PROXIMATE MICROCAPSULES ADAPTED TO RUPTURE IN A MAGNETIC FIELD FOR CONTORLLED RELEASE OF ONE OR MORE AGRICULTURAL CHEMICALS — 805

ACTIVATE THE MAGNETIC FIELD GENERATING DEVICE — 810

FIG. 8

MICROCAPSULES ADAPTED TO RUPTURE IN A MAGNETIC FIELD

CROSS-REFERENCE TO RELATED APPLICATION

This patent application is a divisional application of pending U.S. patent application Ser. No. 13/283,734, filed Oct. 28, 2011, entitled "MICROCAPSULES ADAPTED TO RUPTURE IN A MAGNETIC FIELD", which is hereby incorporated herein by reference in its entirety.

BACKGROUND OF THE INVENTION

1. Field of Invention

The present invention relates in general to the production and use of formulations for the controlled release of agricultural chemicals. More particularly, the present invention relates to the production and use of microcapsules adapted to rupture in a magnetic field for the controlled release of agricultural chemicals.

2. Background Art

In recent years, considerable effort has been expended to coat fertilizers, pesticides and other agricultural chemicals with polymer coatings which will permit a controlled release of the material upon application to plants, soil or the like in a field environment. The shift to polymer-coated agricultural chemicals is driven by myriad reasons, including material handling safety, ecological concerns and economics.

While conventional polymer-coated agricultural chemicals permit a controlled release of the material upon application, the release typically begins at the time of application. Once a conventional polymer-coated agricultural chemical is applied, the start of release is substantially immediate and cannot be altered. Moreover, the release typically occurs everywhere within an application zone where a conventional polymer-coated agricultural chemical is applied irrespective of whether or not the release is desired at a particular location within the application zone.

SUMMARY OF THE INVENTION

According to some embodiments of the present invention, microcapsules adapted to rupture in a magnetic field provide controlled release of agricultural chemicals. The microcapsules, which may be applied to soil, seeds and/or plants, each have a shell that encapsulates an agricultural chemical, such as a fertilizer, herbicide or insecticide. One or more organosilane-coated magnetic nanoparticles is/are covalently bound into the shell of each microcapsule. For example, (3-aminopropyl) trimethylsilane-coated magnetite nanoparticles may be incorporated into the shell of a urea-formaldehyde (UF) microcapsule during in situ polymerization. In one embodiment, microcapsules encapsulating a fertilizer are applied during seed planting. Controlled release is subsequently triggered after an appropriate period of dormancy by positioning a magnetic field generating device proximate the microcapsules to generate a magnetic field sufficient to rupture the microcapsule shells through magnetic stimulation of the organosilane-coated magnetic nanoparticles. The ruptured microcapsule shells release the fertilizer. The controlled release may occur at one or more selected locations within an application zone based on the positioning of the magnetic field generated by the magnetic field generating device. Hence, the farmer can control where and when the released occurs.

The foregoing and other features and advantages of the present invention will be apparent from the following more particular description of some embodiments of the present invention, as illustrated in the accompanying drawings.

BRIEF DESCRIPTION OF THE DRAWINGS

The preferred exemplary embodiments of the present invention will hereinafter be described in conjunction with the appended drawings, where like designations denote like elements.

FIG. 7 is a flow diagram illustrating a method of preparing an enhanced seed in accordance with some embodiments of the present invention.

FIG. 8 is a flow diagram illustrating a method of triggering controlled release of one or more agricultural chemicals from microcapsules adapted to rupture in a magnetic field in accordance with some embodiments of the present invention.

DETAILED DESCRIPTION

Figure 1:
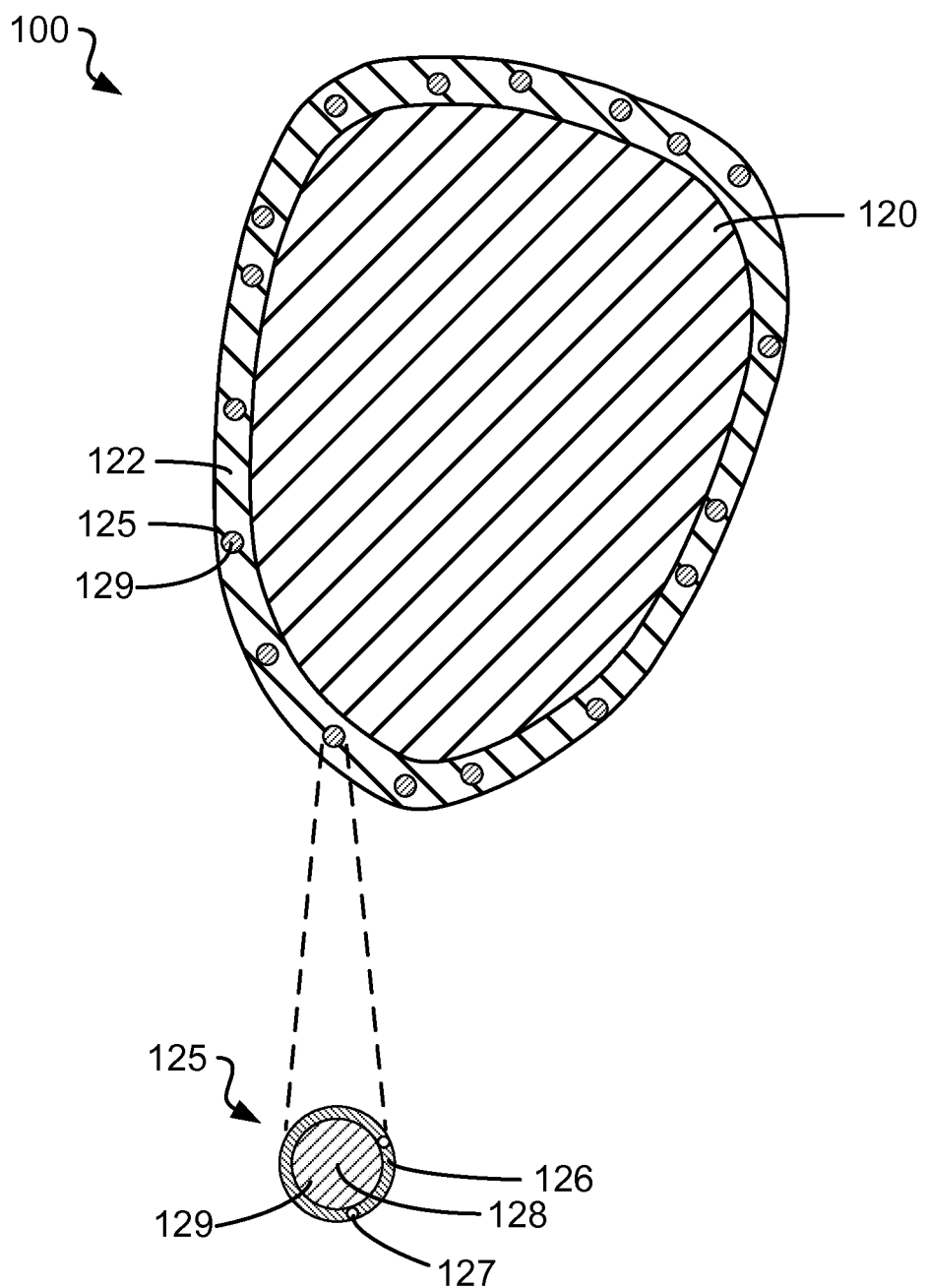
FIG. 1 is a cross-sectional view of an enhanced seed coated with microcapsules adapted to rupture in a magnetic field for controlled release of one or more agricultural chemicals in accordance with some embodiments of the present invention.

According to some embodiments of the present invention, microcapsules adapted to rupture in a magnetic field provide controlled release of agricultural chemicals. The microcapsules, which may be applied to soil, seeds and/or plants, each have a shell that encapsulates an agricultural chemical, such as a fertilizer, herbicide or insecticide. One or more organosilane-coated magnetic nanoparticles is/are covalently bound into the shell of each microcapsule. For example, (3-aminopropyl) trimethylsilane-coated magnetite nanoparticles may be incorporated into the shell of a urea-formaldehyde (UF) microcapsule during in situ polymerization. In one embodiment, microcapsules encapsulating a fertilizer are applied during seed planting. Controlled release is subsequently triggered after an appropriate period of dormancy by positioning a magnetic field generating device proximate the microcapsules to generate a magnetic field sufficient to rupture the microcapsule shells through magnetic stimulation of the organosilane-coated magnetic nanoparticles. The ruptured microcapsule shells release the fertilizer. The controlled release may occur at one or more selected locations within an application zone based on the positioning of the magnetic field generated by the magnetic field generating device. Hence, the farmer can control where and when release occurs.

The seeds and plants with which the microcapsules in accordance with some embodiments of the present invention are useful can be of any species. However, they are preferably plant species that are agronomically important. Of particular importance are barley, canola/rapeseed, corn, cotton, crucifers, curcubits, oats, peanut, potato, rice, rye, sorghum, soybean, sugar beet, sugarcane, sunflower, tobacco, tomato, wheat, as well as other vegetable and leaf crops.

The microcapsules in accordance with some embodiments of the present invention can be applied to seeds, soils and/or plants in the form of a suspension; emulsion; slurry of particles in an aqueous medium (e.g., water); wettable powder; wettable granules (dry flowable); and dry granules. Optionally, the microcapsules in accordance with some embodiments of the present invention may be of differing types (e.g., having different payload types and/or having different microcapsule characteristics so as to rupture at different magnetic field strengths) that can be mixed together and then applied to seeds, soil and/or plants in one of the forms described above. This option makes it possible to release different agricultural chemicals at different points in time, release the same agricultural chemicals at different points in time, or to release different agricultural chemicals at the same point in time.

In general, the "one or more agricultural chemicals" encapsulated within the microcapsules may include one or more fertilizers, pesticides (e.g., herbicides, insecticides, fungicides, rodenticides, and biocides), other crop protection agents (CPAs), and combinations thereof. Preferably, the "one or more agricultural chemicals" encapsulated within the microcapsules include at least one fertilizer and/or at least one herbicide.

As utilized herein a "fertilizer" is any organic or inorganic material of natural or synthetic origin that is conventionally added to soil, seeds, and/or plants to supply one or more plant nutrients. In general, fertilizers typically supply one or more macronutrients and/or one or more micronutrients. Macronutrients include, for example, nitrogen (N), phosphorous (P), potassium (K), calcium (Ca), magnesium (Mg), and sulfur (S). Micronutrients include, for example, boron (B), chlorine (Cl), copper (Cu), iron (Fe), manganese (Mn), molybdenum (Mo), and zinc (Zn).

Organic fertilizers are composed of organic material (plant or animal). Examples of commercially available organic fertilizers include, but are not limited to, manure, worm castings, compost, and seaweed.

Inorganic fertilizers are composed of inorganic material, such as synthetic chemicals and/or minerals. Examples of commercially available inorganic fertilizers include, but are not limited to, N-source fertilizers such as anhydrous ammonia, urea-ammonium nitrate (UAN), urea, ammonium nitrate, ammonium sulfate, sodium nitrate, and calcium cyanamide; P-source fertilizers such as ammonium phosphates (e.g., mono-ammonium phosphate (MAP), di-ammonium phosphate (DAP), and ammonium polyphosphate (APP)), triple (concentrated) superphosphate, normal (ordinary) superphosphate, phosphoric acid, and pulverized phosphate rock; K-source fertilizers such as potassium chloride, potassium sulfate, and potassium magnesium sulfate; and mixed fertilizers (also referred to as compound fertilizers) such as granular homogeneous NPK fertilizers, NPK fertilizers containing significant amounts of secondary and micronutrients, bulk blends containing prescription mixtures of NPK and other essential nutrients formulated for specific geographic areas, and liquid mixed fertilizers (fluid mixes of NP, NS, KS, NPK, NPKS, and the like).

As utilized herein a "pesticide" is a substance or mixture of substances intended for preventing, destroying, controlling, repelling or mitigating any pest. Pests include any undesired insects, plants, plant pathogens, mollusks, birds, mammals, fish, and microbes. Pesticides include, but are not limited to, herbicides, insecticides, fungicides, rodenticides, and biocides.

As utilized herein an "herbicide" is a type of pesticide used to kill unwanted plants, such as weeds, grasses, and the like. Examples of commercially available herbicides include, but are not limited to, phenoxy herbicides such as 2,4-Dichlorophenoxyacetic acid (2,4-D), glyphosate, and triazines such as atrazine. 2,4-D is the most widely used herbicide in the world. Glyphosate (N-(phosphonomethyl)glycine) is the most widely used herbicide in the United States.

In modern agriculture, it is generally desirable to apply controlled quantities of nutrients to fields in order to enhance crop quality and yield. Nutrient-rich fertilizers are typically applied at the field's surface, where the fertilizer is absorbed into the soil, and some portion of the fertilizer reaches the crop's root system to support growth. This is not an efficient technique for distributing nutrients because the soil itself prevents the delivery of a large portion of the nutrients to the roots. This in turn results in larger or more potent fertilizer applications, ultimately increasing environmental damage due to run-off and groundwater pollution. Therefore, there exists a need for an enhanced mechanism to deliver nutrients directly to the root system without so much reliance on the soil as the delivery vehicle.

Myriad controlled-release nutrient products exist on the market. In general, conventional controlled-release nutrient products allow the nutrients to begin releasing the fertilizer directly upon application, followed by a small, steady release until exhaustion of the fertilizer. Unfortunately, this is also an inefficient technique for distributing nutrients. Because conventional controlled-release nutrient products are typically applied with crop seeds, conventional controlled-release nutrient products typically begin releasing nutrients before the seeds have begun to germinate, resulting in lost fertilizer.

Figure 3:
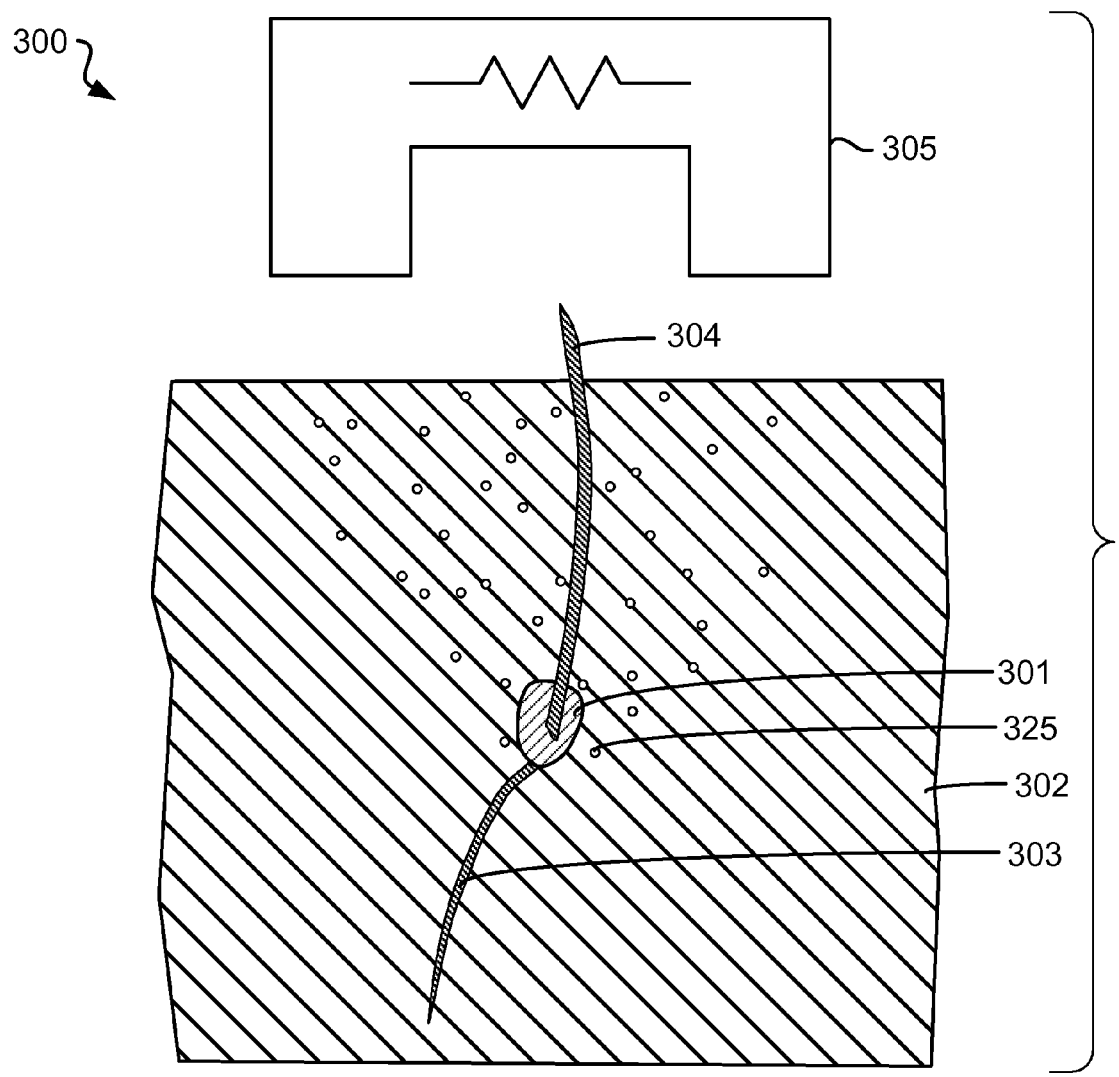
FIG. 3 is a cross-sectional view of a crop field site that includes a conventional seed planted in soil and microcapsules adapted to rupture in a magnetic field and applied to the soil, as well as a magnetic field generating device in accordance with some embodiments of the present invention. Once the conventional seed has germinated and sprouted, as illustrated in the embodiment shown in FIG. 3, the magnetic field generating device is positioned proximate the microcapsules to generate a magnetic field sufficient to rupture the microcapsules and, thereby, release one or more agricultural chemicals in accordance with some embodiments of the present invention.
Figure 9:
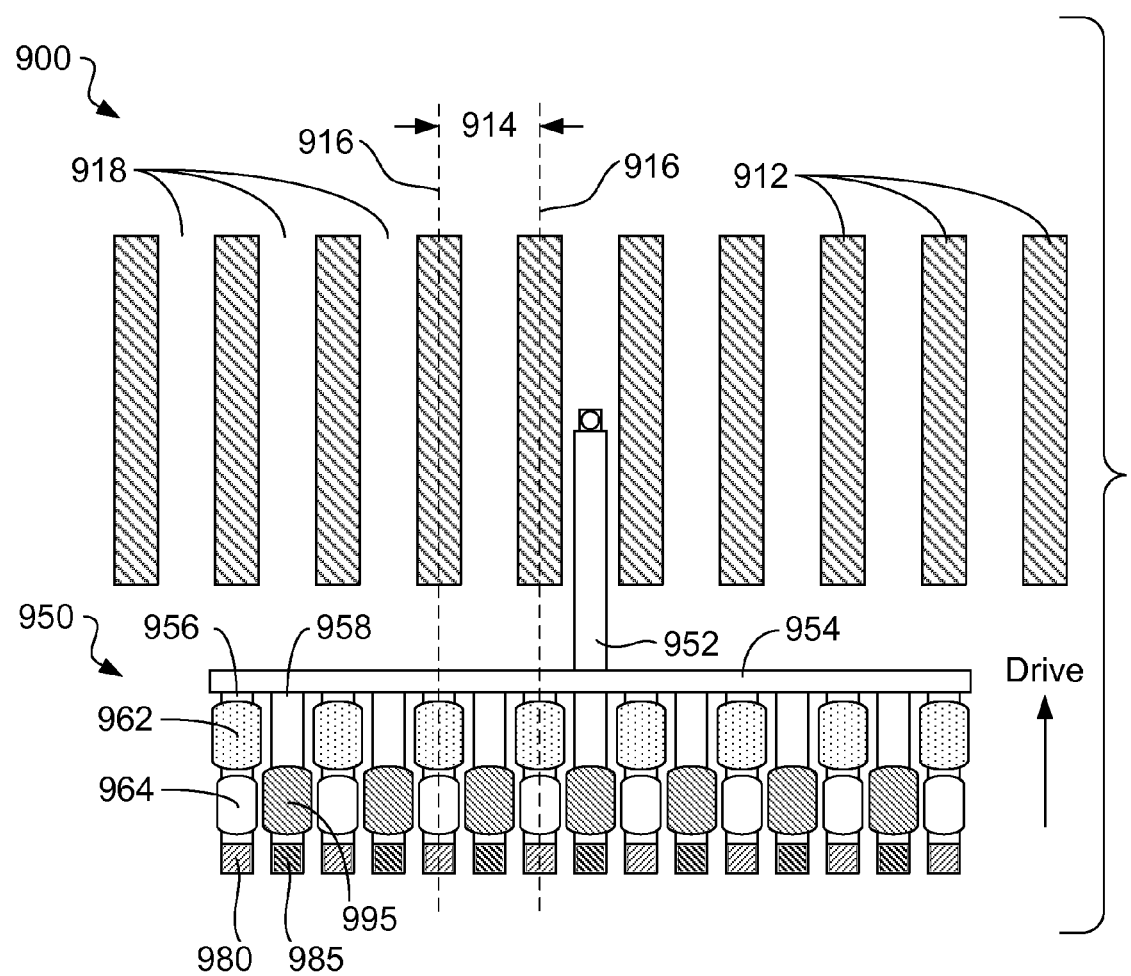
FIG. 9 is a plan view illustrating a row crop and a farm implement apparatus for use with microcapsules adapted to rupture in a magnetic field for controlled release of one or more agricultural chemicals in accordance with some embodiments of the present invention.

In accordance with some embodiments of the present invention, these shortfalls of the prior art (i.e., reliance on soils as the delivery vehicle and nutrient waste due to premature release) are overcome by providing an enhanced mechanism that allows one or more nutrients in a controlled release formulation to be applied during seed planting, and then allows a full release of the nutrients to be triggered after a period of dormancy. For example, some embodiments of the present invention incorporate magnetic nanoparticles into the shell of a urethane-based microcapsule with a nutrient payload at the microcapsule core. The microcapsules may be applied with the crop being planted, for example, resulting in nutrient-loaded microcapsules being in close proximity to each seed. Such an embodiment is illustrated in FIG. 3, and an exemplary apparatus for its application and trigger is illustrated in FIG. 9. After a dormant period, the nutrient payload may be released under application of an external magnetic field, which ruptures the microcapsule shell. In this way, the nutrients may be delivered in full to each individual seed. This enhanced mechanism reduces the amount of nutrients applied and reduces nutrient waste, resulting in cost savings and improved crop performance.

Also, insecticides and herbicides (e.g., phenoxy herbicides used for broad-leaf weed control) exist on the market that can cause unwanted damage to certain crops located in drift areas (e.g., a crop row adjacent to where the insecticide or herbicide is applied). Soybeans, potatoes, and other vegetable crops are particularly susceptible to such damage. Therefore, there exists a need to mitigate drift-area crop damage when utilizing insecticides and/or herbicides, for instance, when treating the areas between crop rows for pests and weeds without affecting the crops themselves.

In accordance with some embodiments of the present invention, drift-area crop damage is mitigated by providing an enhanced mechanism that allows one or more insecticides and/or herbicides in a controlled release formulation to be precisely applied and easily triggered. For example, some embodiments of the present invention incorporate magnetic nanoparticles into the shell of a urethane-based microcapsule with an insecticide payload and/or an herbicide payload at the microcapsule core. The microcapsules are designed to respond to an external magnetic field trigger and rupture. The microcapsules may be applied to the areas between the crop rows, for example, during the planting of the crop (e.g., via a liquid dispersal device attached to a conventional planter) and triggered at a later time with a suitable magnetic field. An exemplary apparatus for application and trigger of such an embodiment is illustrated in FIG. 9. In this manner, the volume of insecticide and/or herbicide applied may be reduced, resulting in both cost savings and a smaller environmental impact. In an alternative embodiment, the microcapsules may be broadly applied and then precision triggered between the crop rows. This alternative embodiment permits use of a conventional application technology.

Figure 2:
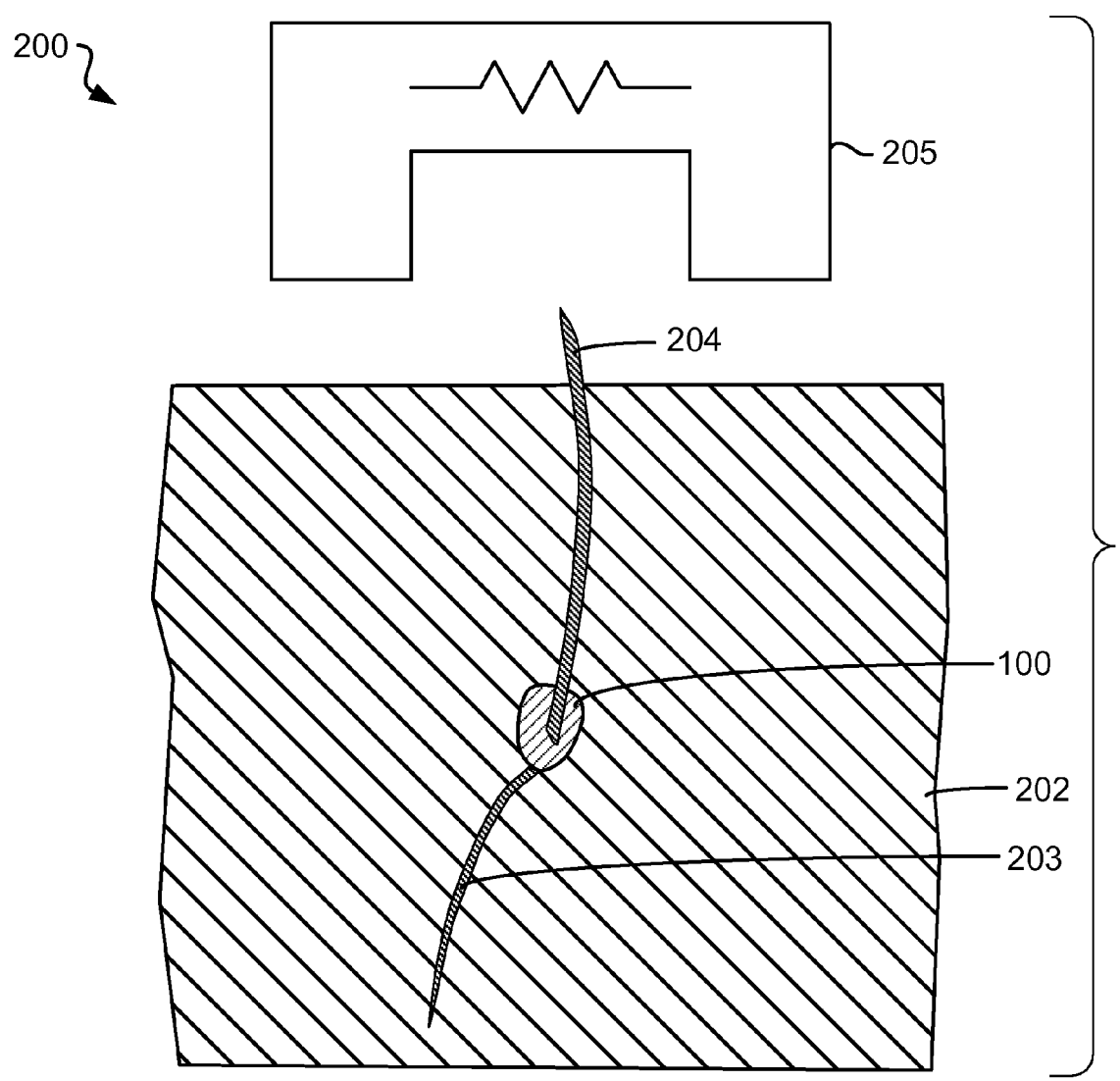
FIG. 2 is a cross-sectional view of a crop field site that includes the enhanced seed shown in FIG. 1 planted in soil, as well as a magnetic field generating device in accordance with some embodiments of the present invention. Once the enhanced seed has germinated and sprouted, as illustrated in the embodiment shown in FIG. 2, the magnetic field generating device is positioned proximate the enhanced seed to generate a magnetic field sufficient to rupture the microcapsules coating the enhanced seed and, thereby, release one or more agricultural chemicals in accordance with some embodiments of the present invention.

Also, an enhanced seed coated with microcapsules in accordance with some embodiments of the present invention can be instructed to release one or more agricultural chemicals (e.g., fertilizers, herbicides, insecticides, and combinations thereof) on demand. For example, by incorporating magnetic nanoparticles into the shell of a urethane-based microcapsule, encapsulating one or more agricultural chemicals in the core of the microcapsule, and coating a seed with such microcapsules in accordance with some embodiments of the present invention, the agricultural chemicals can be released from the microcapsules under application of an external magnetic field (i.e., "on demand"). Such an embodiment is illustrated in FIGS. 1 and 2, and an exemplary apparatus for its application and trigger is illustrated in FIG. 9. Application of the magnetic field ruptures the microcapsule shell, which in turn releases the agricultural chemicals.

Figure 4:
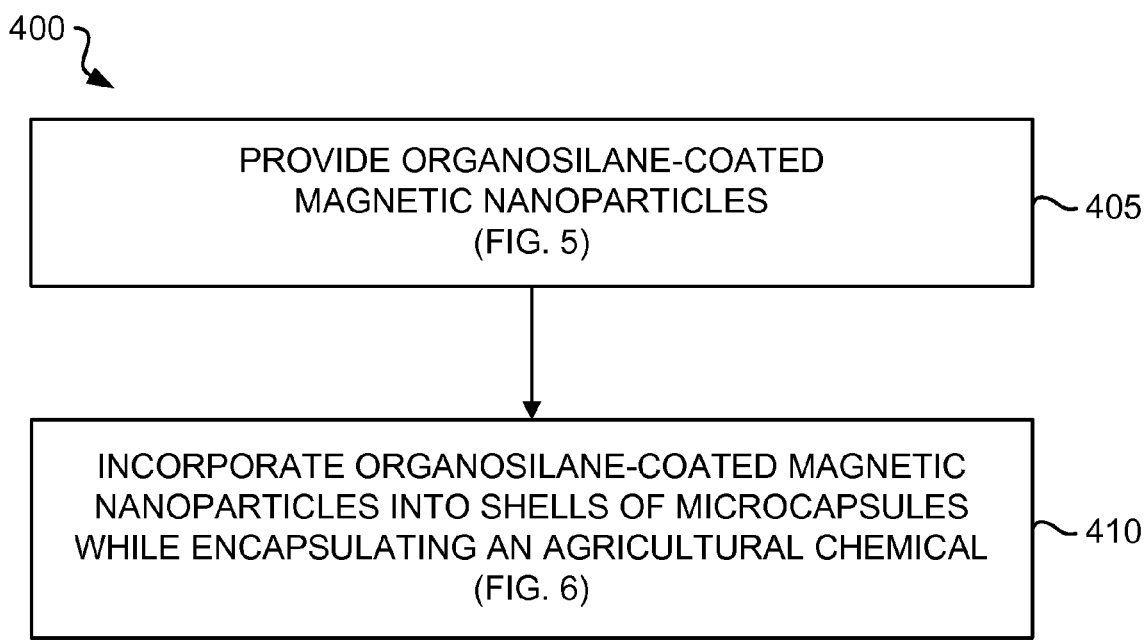
FIG. 4 is a flow diagram illustrating a method of preparing microcapsules adapted to rupture in a magnetic field for controlled release of one or more agricultural chemicals in accordance with some embodiments of the present invention.

In accordance with some embodiments of the present invention, microcapsules adapted to rupture in a magnetic field for controlled release of one or more agricultural chemicals are prepared utilizing a multi-step process. This multi-step process is illustrated in FIG. 4. Initially, organosilane-coated magnetic nanoparticles are provided. This initial step corresponds to step 405 in FIG. 4, an example of which is illustrated in greater detail in FIG. 5. Then, the organosilane-coated magnetic nanoparticles are incorporated into shells of microcapsules while encapsulating one or more agricultural chemicals. This subsequent step corresponds to step 410 in FIG. 4, an example of which is illustrated in greater detail in FIG. 6.

In accordance with some embodiments of the present invention, an organo trialkoxysilane, such as aminopropyltriethoxysilane, is reacted with a mild acid (e.g., acetic acid, hydrochloric acid, formic acid) in an aqueous solution to form a hydrolyzed silane. This step, which corresponds to step 505 in FIG. 5, may be performed at ambient temperature or elevated temperatures to increase the reaction kinetics of the silane formation. Additionally, the solvent used in this step may be, for example, tetrahydrofuran, ethanol or methanol. Once the silane is formed, magnetic nanoparticles are added to the solution and mixed. This step corresponds to step 510 in FIG. 5. The magnetic nanoparticles may be, for example, $Fe_3O_4$ (also referred to as "magnetite") prepared using conventional techniques known to those skilled in the art.

An outline of an example of this subsequent step (corresponding to step 510 in FIG. 5) is set forth in Equation 1 below.

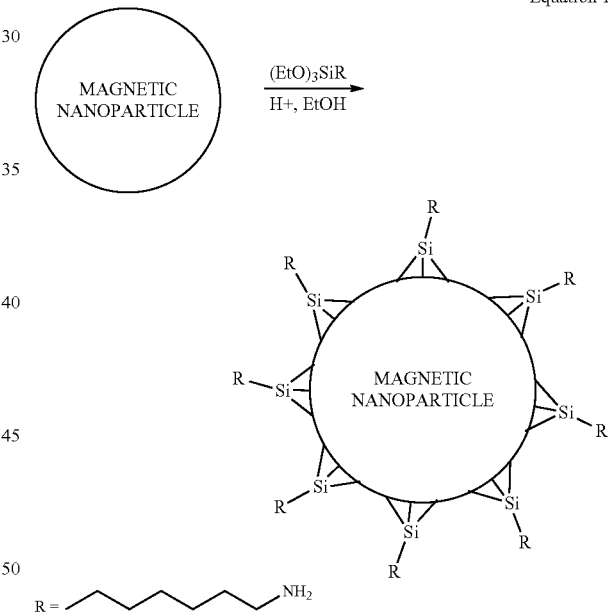

Equation 1

This then results in the functionalization of a magnetic nanoparticle, which can be then covalently bound into the shell of a urea-formaldehyde (UF) microcapsule while encapsulating one or more agricultural chemicals. This subsequent step corresponds to step 410 in FIG. 4, which step is illustrated in greater detail in FIG. 6. One or more agricultural chemicals can be incorporated into the core of these microcapsules through conventional microcapsule fabrication processes (e.g., in situ polymerization of a urea-formaldehyde (UF) microcapsule shell around a core material to encapsulate that material) known to those skilled in the art.

Also, in accordance with some embodiments of the present invention, an enhanced seed may be prepared by coating microcapsules adapted to rupture in a magnetic field for controlled release of one or more agricultural chemicals (e.g., prepared by the multi-step process illustrated in FIG. 4) onto a conventional seed. This corresponds to the method illustrated in FIG. 7.

Still further, in accordance with some embodiments of the present invention, a controlled release of one or more agricultural chemicals from an enhanced seed coated with microcapsules adapted to rupture in a magnetic field (e.g., prepared by the process illustrated in FIG. 7) may be triggered by applying a magnetic field to the enhanced seed. Application of a sufficiently strong magnetic field (e.g., 2.5 kA/m or 31 Oe) causes magnetic particles covalently bound into the shell of the microcapsules to rotate at an accelerated rate, thereby rupturing the outer shell of the microcapsules and, in turn, releasing the agricultural chemical.

FIG. 1 is a cross-sectional view of an enhanced seed 100 coated with microcapsules 125 adapted to rupture in a magnetic field for controlled release of one or more agricultural chemicals in accordance with some embodiments of the present invention.

For example, the enhanced seed 100 may be prepared in accordance with some embodiments of the present invention by coating a conventional crop seed 120 with microcapsules 125 adapted to rupture in a magnetic field for controlled release of one or more agricultural chemicals. The crop seed 120 (prior to modification by coating with the microcapsules 125 in accordance with some embodiments of the present invention, as described below with reference to FIG. 7) is conventional. The crop seed 120 may be selected from any number of commercially available seed products, including "treated" seeds. For example, commercially available seed products that are suitable for use as the crop seed 120 include, but are not limited to corn, cotton, soybean, and wheat.

The microcapsules 125 can be applied "neat" to each conventional crop seed 120, that is without diluting or additional components present. However, the microcapsules 125 are typically applied to each conventional crop seed 120 in the form of a coating 122 that may contain one or more other desirable components including, but not limited to, liquid diluents, binders, fillers for protecting the seeds from stress conditions, and other ingredients to improve flexibility, adhesion and/or spreadability of the coating 122. In some situations, it may be desirable to add drying agents such as calcium carbonate, kaolin or bentonite clay, perlite, diatomaceous earth or any other adsorbent material. Use of such components in seed treatments is known in the art. See, e.g., U.S. Pat. Nos. 5,876,739 and 6,858,634 B2, which are hereby incorporated herein by reference in their entirety.

Each microcapsule 125 has a shell 126 into which one or more organosilane-coated magnetic nanoparticles 127 is/are covalently bound. The shell 126 of each microcapsule 125 defines a core 128 within which one or more agricultural chemicals 129 is/are encapsulated. In FIG. 1, the core 128 of each microcapsule 125 is illustrated with cross-hatched lines to denote the core 128 is filled with one or more agricultural chemicals 129 (and, optionally, one or more solvents, discussed below). In accordance with some embodiments of the present invention, each microcapsule 125 is a urea-formaldehyde (UF) microcapsule having a UF-based shell 126 into which one or more (3-aminopropyl) trimethylsilane-coated magnetic nanoparticles 127 is/are covalently bound. The UF microcapsule 125 encapsulates one or more agricultural chemicals 129.

In some embodiments of the present invention, the UF microcapsule 125 encapsulates a core solution comprising one or more solvents into which one or more agricultural chemicals is/are dissolved. The one or more solvents may be selected from any number of materials that dissolve the one or more agricultural chemicals. Suitable solvents include, but are not limited to, toluene, ethyl acetate, xylene, acetone, or suitable combinations thereof.

More generally, suitable solvents include, but are not limited to, aromatic hydrocarbons such as xylenes, naphthalenes, or mixtures of aromatics; aliphatic or cycloaliphatic hydrocarbons such as hexane, heptane, and cyclohexane; alkyl esters including alkyl acetates and alkyl phthalates; ketones such as cyclohexanone or acetophenone; chlorinated hydrocarbons; vegetable oils; or mixtures of two or more such solvents.

While the microcapsules 125 in the example above are described in the context of urea-formaldehyde (UF) microcapsules having UF-based shells 126, this particular microcapsule material is merely exemplary. Suitable materials for the shells of the microspheres include, but are not limited to, urea-formaldehyde, vinylidene chloride-acrylonitrile copolymer, polyvinyl alcohol, polyvinyl butyral, polymethylmethacrylate, polyacrylonitrile, polyvinylidene chloride, polysulfone, and the like. The one or more agricultural chemicals 129 is/are encapsulated within the shells 126 to form microcapsules 125 using techniques known to those skilled in the art, such as an in-situ polymerization method, a coacervation method, or an interfacial polymerization method—these conventional techniques, however, are modified in accordance with the preferred embodiment of the present invention so that one or more organosilane-coated magnetic nanoparticles 127 is/are covalently bound into the shell 126 of each microcapsule 125. For example, as described below with reference to FIG. 6, the microcapsules 125 may be produced by in situ polymerization of urea-formaldehyde shells 126 around the one or more agricultural chemicals 129.

FIG. 2 is a cross-sectional view of a crop field site 200 that includes the enhanced seed 100 shown in FIG. 1 planted in soil 202, as well as a magnetic field generating device 205 in accordance with some embodiments of the present invention. At a suitable time, for example, after the enhanced seed 100 has germinated and sprouted, as illustrated in the embodiment shown in FIG. 2, the magnetic field generating device 205 is positioned proximate the enhanced seed 100 to generate a magnetic field sufficient to rupture the microcapsules (125 in FIG. 1) coating the enhanced seed 100 and, thereby, release one or more agricultural chemicals in accordance with some embodiments of the present invention.

In the embodiment shown in FIG. 2, as denoted by a root 203 and a sprout 204 emerging from the enhanced seed 100, the release is triggered after the enhanced seed 100 has germinated and sprouted. This timing is exemplary. The release may be triggered at any suitable time relative to the planting of the enhanced seed 100, preferably after an appropriate period of dormancy. Release of a fertilizer encapsulated in accordance with some embodiments of the present invention, for example, may be triggered after an appropriate period of dormancy that is selected to reduce nutrient waste. Release of an herbicide or insecticide in accordance with some embodiments of the present invention, for example, may be triggered after an appropriate period of dormancy that is selected to avoid exposing the seed to what would be a "toxic level" of the herbicide or insecticide at an earlier stage of growth.

The magnetic field generated by the magnetic field generating device 205 is sufficient to rupture the microcapsule shells (126 in FIG. 1) through magnetic stimulation of the organosilane-coated magnetic nanoparticles (127 in FIG. 1). Application of a sufficiently strong high-frequency magnetic field causes the organosilane-coated magnetic nanoparticles embedded in the microcapsule shells to rotate and/or vibrate at an accelerated rate, thereby rupturing the microcapsule shells of the microcapsules and, in turn, releasing the encapsulated one or more agricultural chemicals (129 in FIG. 1).

Preferably, the high-frequency magnetic field applied to the enhanced seed 100 by the magnetic field generating device 205 has a frequency of approximately 50-100 kHz and a strength of approximately 2.5 kA/m or 31 Oe. The one or more agricultural chemicals is/are released from the core (128 in FIG. 1) of each ruptured microcapsule shell.

The magnetic field generating device 205 is conventional, and typically includes a power supply, a functional generator, an amplifier, a multi-loop coil, and a cooling system. Preferably, the temperature of the magnetic field generating device 205 is controlled by cycling cooling water at 25° C. through the cooling system.

FIG. 3 is a cross-sectional view of a crop field site 300 that includes a conventional seed 301 planted in soil 302 and microcapsules 325 adapted to rupture in a magnetic field applied to the soil 302, as well as a magnetic field generating device 305 in accordance with some embodiments of the present invention. The microcapsules 325 applied to the soil 302 in FIG. 3 (e.g., applied by the farm implement apparatus illustrated in FIG. 9) correspond to the microcapsules 125 coated onto the seed in FIG. 1. At a suitable time, for example, after the conventional seed 301 has germinated and sprouted, as illustrated in the embodiment shown in FIG. 3, the magnetic field generating device 305 is positioned proximate the conventional seed 301 to generate a magnetic field sufficient to rupture the microcapsules 325 and, thereby, release one or more agricultural chemicals in accordance with some embodiments of the present invention.

In the embodiment shown in FIG. 3, as denoted by a root 303 and a sprout 304 emerging from the conventional seed 301, the release is triggered after the conventional seed 301 has germinated and sprouted. This timing is exemplary. The release may be triggered at any suitable time relative to the planting of the conventional seed 301, preferably after an appropriate period of dormancy. Release of a fertilizer encapsulated in accordance with some embodiments of the present invention, for example, may be triggered after an appropriate period of dormancy that is selected to reduce nutrient waste. Release of an herbicide or insecticide in accordance with some embodiments of the present invention, for example, may be triggered after an appropriate period of dormancy that is selected to avoid exposing the seed to what would be a "toxic level" of the herbicide or insecticide at an earlier stage of growth.

The magnetic field generated by the magnetic field generating device 305 is sufficient to rupture the microcapsule shells (126 in FIG. 1) through magnetic stimulation of the organosilane-coated magnetic nanoparticles (127 in FIG. 1). Application of a sufficiently strong high-frequency magnetic field causes the organosilane-coated magnetic nanoparticles embedded in the microcapsule shells to rotate and/or vibrate at an accelerated rate, thereby rupturing the microcapsule shells of the microcapsules and, in turn, releasing the encapsulated one or more agricultural chemicals (129 in FIG. 1).

Preferably, the high-frequency magnetic field applied to the conventional seed 301 by the magnetic field generating device 305 has a frequency of approximately 50-100 kHz and a strength of approximately 2.5 kA/m or 31 Oe. The one or more agricultural chemicals is/are released from the core (128 in FIG. 1) of each ruptured microcapsule shell. In FIG. 3, the core of each microcapsule 325 is illustrated without cross-hatched lines to denote the core is no longer filled with one or more agricultural chemicals (129 in FIG. 1).

The magnetic field generating device 305 is conventional, and typically includes a power supply, a functional generator, an amplifier, a multi-loop coil, and a cooling system. Preferably, the temperature of the magnetic field generating device 305 is controlled by cycling cooling water at 25° C. through the cooling system.

FIG. 4 is a flow diagram illustrating a method 400 of preparing microcapsules adapted to rupture in a magnetic field for controlled release of one or more agricultural chemicals in accordance with some embodiments of the present invention. In the method 400, the steps discussed below (steps 405-410) are performed. These steps are set forth in their preferred order. It must be understood, however, that the various steps may occur simultaneously.

In accordance with some embodiments of the present invention, the method 400 begins by providing organosilane-coated magnetic nanoparticles (step 405). An example of this step 405 of providing organosilane-coated magnetic nanoparticles is illustrated in greater detail in FIG. 5. The method 400 continues by incorporating the organosilane-coated magnetic nanoparticles into shells of microcapsules while encapsulating one or more agricultural chemicals (step 410). An example of this step 410 of incorporating the organosilane-coated magnetic nanoparticles into shells of microcapsules while encapsulating one or more agricultural chemicals is illustrated in greater detail in FIG. 6.

Figure 5:
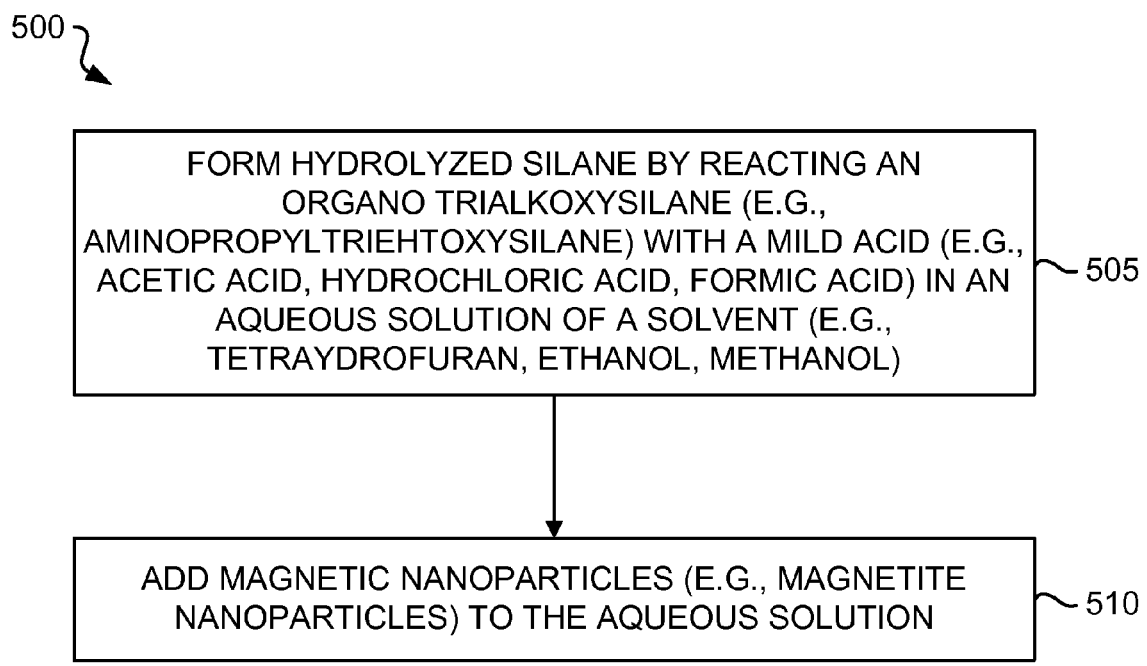
FIG. 5 is a flow diagram illustrating a method of preparing organosilane-coated magnetic nanoparticles in accordance with some embodiments of the present invention.

FIG. 5 is a flow diagram illustrating a method 500 of preparing organosilane-coated magnetic nanoparticles in accordance with some embodiments of present invention. In the method 500, the steps discussed below (steps 505-510) are performed. These steps are set forth in their preferred order. It must be understood, however, that the various steps may occur simultaneously.

In accordance with some embodiments of the present invention, the method 500 begins by reacting an organo trialkoxysilane, such as aminopropyltriethoxysilane, with a mild acid (e.g., acetic acid, hydrochloric acid, formic acid) in an aqueous solution to form a hydrolyzed silane (step 505). This step 505 is performed using standard silane hydrolysis procedures known to those skilled in the art. The hydrolyzed silane formation step 505 may be performed at ambient temperature or elevated temperatures to increase the reaction kinetics of the silane formation. Additionally, the aqueous solution used in the hydrolyzed silane formation step 505 includes a suitable solvent, such as tetrahydrofuran, ethanol or methanol.

One skilled in the art will appreciate that the organo trialkoxysilane reacted in the hydrolyzed silane formation step 505 may be selected from a group of suitable organo trialkoxysilanes including, but not limited to, amine-terminated trialkoxysilanes, vinyl-terminated trialkoxysilanes, and isocyanate-terminated trialkoxysilanes. Examples of additional suitable organo trialkoxysilanes include:
Trimethoxy[3-(methylamino)propyl]silane
[3-(2-Aminoethylamino)propyl]trimethoxysilane
3-(Triethoxysilyl)propyl isocyanate-(3-Trimethoxysilylpropyl)diethylenetriamine Once the hydrolyzed silane is formed in the step 505, the method 500 continues by adding magnetic nanoparticles to the solution (step 510). Preferably, the hydrolyzed silane solution is mixed while the magnetic nanoparticles are added and/or thereafter.

The magnetic nanoparticles may be, for example, $Fe_3O_4$ (also referred to as "magnetite") nanoparticles, cobalt ferrite nanoparticles, or other magnetic nanoparticles known in the art. Preferably, the magnetic nanoparticles have a diameter in the range of approximately 6-25 nm The magnetic nanoparticles are prepared using conventional techniques known to those skilled in the art. For example, magnetite nanoparticles may be prepared using a conventional technique known as the "coprecipitation method." See, for example, the discussion of preparing magnetite nanoparticles using the coprecipitation method in the article to M. Yamaura et al., "Preparation and characterization of (3-aminopropyl) triethoxysilane-coated magnetite nanoparticles," Journal of Magnetism and Magnetic Materials, Vol. 279, pages 210-217, 2004, which is hereby incorporated herein by reference in its entirety.

An example of a conventional technique of preparing magnetite nanoparticles follows. This conventional example is based on an example set forth in the M. Yamaura et al. article. A 5 mol/l NaOH solution is added into a mixed solution of 0.25 mol/l ferrous chloride and 0.5 mol/l ferric chloride (molar ratio 1:2) until obtaining pH 11 at room temperature. The slurry is washed repeatedly with distilled water. Then, the resulting magnetite nanoparticles are magnetically separated from the supernatant and redispersed in aqueous solution at least three times, until obtaining pH 7. The M. Yamaura et al. article reports that a typical average diameter of the resulting magnetite nanoparticles is 12 nm.

Alternatively, the magnetite nanoparticles may be prepared and then coated with (3-aminopropyl)triethoxysilane using the silanization reaction set forth in the M. Yamaura et al. article. That is, the magnetite suspension (i.e., the resulting magnetite nanoparticles redispersed in aqueous solution at least three times, until obtaining pH 7, as discussed above) may be heated with glycerol and 40 ml of a 10% water solution of (3-aminopropyl)triethoxysilane (pH 4.0, adjusted with glacial acetic acid) in a water bath for three hours. The silanization reaction set forth in the M. Yamaura et al. article occurs in two steps. In the first step, the organosilane is placed into an aqueous solution of an acid that acts as a catalyst. The organosilane is hydrolyzed, and a condensation reaction occurs to form a silane polymer. In the hydrolysis reaction, alkoxide groups ($-OC_2H_5$) are replaced by hydroxyl groups ($-OH$) to form reactive silanol groups to produce siloxane bonds ($Si-O-Si$). Alcohol ($C_2H_5OH$) and water are produced as by-products of condensation. In the second step, the polymer associates with the magnetite crystallites (or surface clusters) forming a covalent bond with OH groups. Dehydration as well as adsorption of silane polymers to the metal oxide occurs. In sequence, after magnetic separation, the silanized magnetite particles may be thoroughly washed with distilled water and dried, yielding a fine powder. The M. Yamaura et al. article reports that a typical average diameter of the resulting (3-aminopropyl) triethoxysilane-coated magnetite nanoparticles is 15 nm.

Figure 6:
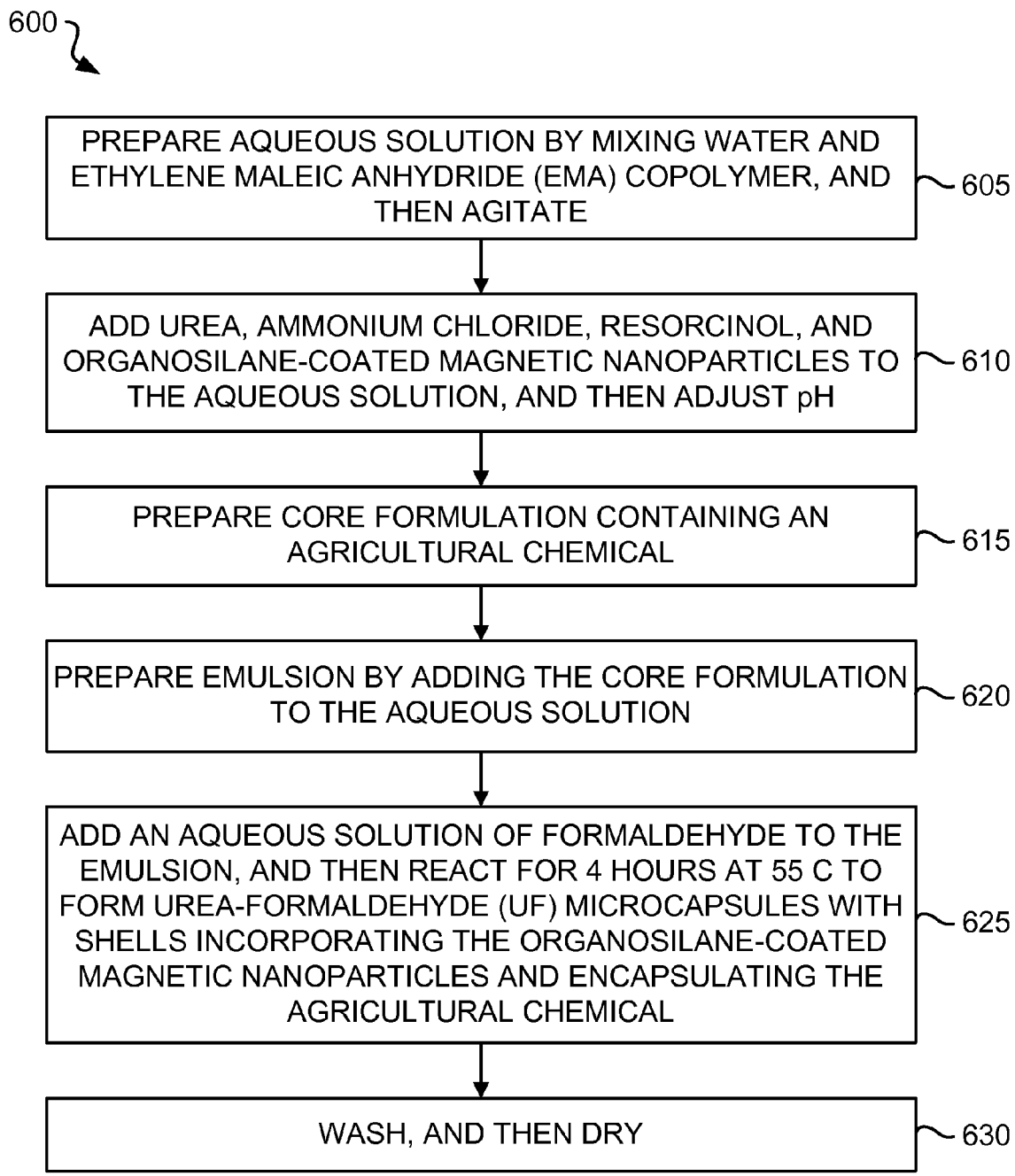
FIG. 6 is a flow diagram illustrating a method of incorporating organosilane-coated magnetic nanoparticles into shells of microcapsules for controlled release of one or more agricultural chemicals in accordance with some embodiments of the present invention.

FIG. 6 is a flow diagram illustrating a method 600 of incorporating organosilane-coated magnetic nanoparticles into shells of microcapsules for controlled release of one or more agricultural chemicals in accordance with some embodiments of present invention. In the method 600, the steps discussed below (steps 605-630) are performed. These steps are set forth in their preferred order. It must be understood, however, that the various steps may occur simultaneously or at other times relative to one another. Moreover, those skilled in the art will appreciate that one or more steps may be omitted.

In accordance with some embodiments of the present invention, conventional microcapsule fabrication processes (e.g., in situ polymerization of urea-formaldehyde (UF) microcapsule shells) may be modified to incorporate the organosilane-coated magnetic nanoparticles so that the nanoparticles are covalently bound into shells of microcapsules and to encapsulate one or more agricultural chemicals. Such conventional fabrication processes are described in E. N. Brown et al., "In situ poly(urea-formaldehyde) microencapsulation of dicyclopentadiene," Journal of Microencapsulation, Vol. 20, No. 6, pages 719-730, 2003 and B. J. Blaiszik et al., "Microcapsules filled with reactive solutions for self-healing materials," Polymer, Vol. 50, pages 990-997, 2009, each of which is hereby incorporated herein by reference in its entirety.

The method 600 begins by preparing an aqueous solution by mixing water and ethylene maleic anhydride (EMA) copolymer, and then agitating the aqueous solution (step 605). For example, 200 ml of deionized water and 50 ml of 2.5 wt % aqueous solution of EMA copolymer may be mixed at room temperature (20-24° C.) in a 1000 ml beaker. The beaker may be suspended in a temperature-controlled water bath on a programmable hotplate monitored with an external temperature probe. The aqueous solution may be agitated with a digital mixer driving a three-bladed, 63.5 mm diameter low-shear mixing propeller placed just above the bottom of the beaker. Preferably, the aqueous solution is agitated at 200-2000 rpm.

Next, the method 600 continues by adding urea, ammonium chloride, resorcinol, and organosilane-coated magnetic nanoparticles to the aqueous solution, and then adjusting the pH (step 610). Preferably, an appropriate amount of organosilane-coated magnetic nanoparticles are added to the aqueous solution such that urea-formaldehyde (UF) microcapsules are fabricated that have a magnetic nanoparticle content of approximately 0.5-20 wt %. For example, while the aqueous solution is under agitation (e.g., at 800 rpm), 5.0 g urea, 0.5 g ammonium chloride, 0.5 g resorcinol, and 1.2 g organosilane-coated magnetic nanoparticles may be added in the aqueous solution. The pH may then be raised from approximately 2.6 to 3.5 by drop-wise addition of sodium hydroxide (NaOH). One or more drops of 1-octanol may be added to eliminate surface bubbles.

In lieu of, or in addition to, adding organosilane-coated magnetic nanoparticles to the aqueous solution during step 610, the nanoparticles may be added to the emulsion during step 625. In either case, an appropriate amount of organosilane-coated magnetic nanoparticles are added such that urea-formaldehyde (UF) microcapsules are fabricated that have a magnetic nanoparticle content of approximately 0.5-20 wt %.

The method 600 continues by preparing a core formulation containing one or more agricultural chemicals (step 615). The core formulation may be a core solution or a core powder. For example, a core solution comprised entirely of one or more agricultural chemicals may be prepared. Alternatively, a core solution may be prepared by dissolving one or more agricultural chemicals in one or more suitable solvents. Suitable solvents include, but are not limited to, toluene, ethyl acetate, xylene, acetone, or suitable combinations thereof. In an alternative to the preparation of a core solution, it may be desirable to prepare the core formulation as a core powder comprised of a powdered form of one or more solid agricultural chemicals.

In Example 1 (a fertilizer-payload embodiment), 60 ml of a core solution comprised of ammonium polyphosphate 10-34-0 is prepared. Ammonium polyphosphate 10-34-0 is a liquid ammonium polyphosphate fertilizer commercially available under the tradename POLY 10 from Potash Corporation of Saskatchewan Inc., Saskatoon, Saskatchewan, Canada. It is not uncommon to use ammonium polyphosphate 10-34-0 as a pop-up fertilizer applied directly in the seed furrow. Typically, ammonium polyphosphate 10-34-0 is applied in pop-up fertilizer applications at rates of 100 lbs/acre. See, for example, the discussion of ammonium polyphosphate 10-34-0 and other conventional fertilizers in M. Alley et al., "Pop-up and/or Starter Fertilizers for Corn," Virginia Cooperative Extension Publication 3002-1438, 2010, which is hereby incorporated herein by reference in its entirety. Hence with respect to Example 1, the microcapsules formed later in the method 600 (i.e., in step 625, described below) will be applied to seeds, soils and/or plants in the form of a suspension; emulsion; slurry of particles in an aqueous medium (e.g., water); wettable powder; wettable granules (dry flowable); and dry granules, so that ultimately the ammonium polyphosphate 10-34-0 fertilizer encapsulated within the microcapsules is applied in the crop field at a rate of approximately 100 lbs/acre.

Both liquid and solid ammonium polyphosphates $[NH_4PO_3]_n$ are commercially available. In an alternative to the preparation of a core solution in step 615 (Example 1), it may be desirable to prepare the core formulation as a core powder comprised of one or more solid ammonium polyphosphates in lieu of, or in addition to, ammonium polyphosphate 10-34-0. In this way, a crystalline powder of solid ammonium polyphosphate may be encapsulated in lieu of, or in addition to, ammonium polyphosphate 10-34-0.

In Example 2 (an herbicide-payload embodiment), 60 g of a core powder comprised of glyphosate powder is prepared. As mentioned above, glyphosate (N-(phosphonomethyl)glycine) is the most widely used herbicide in the United States. Glyphosate, which is a white crystalline powder, is commercially available in solid form from chemical suppliers, such as Sigma-Aldrich, Saint Louis, Mo. Typically, glyphosate is applied in herbicide applications at different solution strengths (e.g., 120, 240, 360, 480 and 680 g active ingredient per liter) at solution rates of 3-12 liters/hectare. Therefore, at the most common solution strength of 360 g active ingredient per liter, glyphosate is applied at a rate of about 437-1748 g/acre. Hence with respect to Example 2, the microcapsules formed later in the method 600 (i.e., in step 625, described below) will be applied to seeds, soils and/or plants in the form of a suspension; emulsion; slurry of particles in an aqueous medium (e.g., water); wettable powder; wettable granules (dry flowable); and dry granules, so that ultimately the glyphosate herbicide encapsulated within the microcapsules is applied in the crop field at a rate of approximately 437-1748 g/acre.

Glyphosate is marketed in different solution strengths under numerous tradenames. For example, a water-based solution containing glyphosate, a surfactant, and other substances is marketed under the tradename Roundup available from Monsanto Company, St. Louis, Mo. In an alternative to the preparation of a core powder in step 615 (Example 2), it may be desirable to prepare the core formulation as a core solution comprised of one or more glyphosate solutions in lieu of, or in addition to, glyphosate powder.

This core formulation preparation step 615 (e.g., Example 1 or 2) may be performed at any time prior to the emulsion preparation step 620, described below.

Next, the method 600 continues by preparing an emulsion by adding the core formulation to the aqueous solution (step 620). For example, a slow stream of 60 ml of a core solution (prepared in step 615) may be added to the aqueous solution (prepared in step 610) to form an emulsion. The emulsion is allowed to stabilize, preferably for about 10 min.

Then, the method 600 continues by adding an aqueous solution of formaldehyde to the emulsion, and then reacted for 4 hours at 55° C. to form urea-formaldehyde (UF) microcapsules with shells incorporating the organosilane-coated magnetic nanoparticles and encapsulating one or more agricultural chemicals (step 625). For example, after stabilization of the emulsion (in step 620), 12.7 g of 37 wt % aqueous solution of formaldehyde (this solution is also known as "formalin") may be added to the emulsion (prepared in step 620) to obtain a 1:1.9 molar ratio of formaldehyde to urea. The resulting emulsion may be covered and heated at a rate of 1° C./min to the target temperature of 55° C. After 4 hours of continuous agitation (e.g., at 800 rpm), the mixer and hot plate may be switched off. Once cooled to ambient temperature, the suspension of microcapsules may be separated under vacuum with a coarse-fitted filter.

Finally, the method 600 concludes by washing and then drying the microcapsules (step 630). For example, the microcapsules (prepared in step 625) may be rinsed with deionized water and air dried for 24-48 hours. A sieve may be used to aid in the separation of the microcapsules. Alternatively, the microcapsules may be retained in the emulsion, which may be applied "as-is" to seeds, soils and/or plants.

FIG. 7 is a flow diagram illustrating a method of preparing an enhanced seed in accordance with some embodiments of present invention. In the method 700, the steps discussed below (steps 705-710) are performed. These steps are set forth in their preferred order. It must be understood, however, that the various steps may occur simultaneously or at other times relative to one another. Moreover, those skilled in the art will appreciate that one or more steps may be omitted.

The method 700 begins by providing microcapsules adapted to rupture in a magnetic field for controlled release of one or more agricultural chemicals (step 705). For example, such microcapsules may be prepared in accordance to the method 600, described above with reference to FIG. 6. The microcapsule preparation step may be performed any time prior to the coating step 710, described below.

The method 700 concludes by coating seeds with the microcapsules (step 710). The microcapsules can be applied "neat" to each seed, that is, without diluting or additional components present. However, the microcapsules are typically applied to each seed in the form of a coating that may contain one or more other desirable components including, but not limited to, liquid diluents, binders, fillers for protecting the seeds from stress conditions, and other ingredients to improve flexibility, adhesion and/or spreadability of the coating. In some situations, it may be desirable to add drying agents such as calcium carbonate, kaolin or bentonite clay, perlite, diatomaceous earth or any other adsorbent material.

FIG. 8 is a flow diagram illustrating a method 800 of triggering controlled release of one or more agricultural chemicals from microcapsules adapted to rupture in a magnetic field in accordance with some embodiments of the present invention. In the method 800, the steps discussed below (steps 805-810) are performed. These steps are set forth in their preferred order. It must be understood, however, that the various steps may occur simultaneously or at other times relative to one another. Moreover, those skilled in the art will appreciate that one or more steps may be omitted.

The method 800 begins by positioning a magnetic field generating device proximate microcapsules adapted to rupture in a magnetic field for controlled release of one or more agricultural chemicals (step 805). For example, the magnetic field generating device 205 (shown in FIG. 2) may be positioned proximate an enhanced seed 100 (shown in FIGS. 1 and 2).

Then, the method 800 continues by activating the magnetic field generating device (step 810). For example, activation of the magnetic field generating device may be accomplished by initiating the flow of electrical current through the device's multi-loop coil to generate a magnetic field having the desired strength. For example, as a consequence of activation of the magnetic field generating device, the microcapsule shells rupture, the ruptured microcapsules release the one or more agricultural chemicals encapsulated in the microcapsules.

FIG. 9 is a plan view illustrating a row crop 900 and a farm implement apparatus 950 for use with microcapsules adapted to rupture in a magnetic field for controlled release of one or more agricultural chemicals in accordance with some embodiments of the present invention.

The row crop 900 has a plurality of rows 912 spaced apart from one another by row spacing 914. Also shown in FIG. 9 are the areas between the rows 912 of crop 900, such areas being designated area 918. Row crop 900 may comprise rows of any crop such as corn, potato, soybean, and wheat, as well as other vegetable and leaf crops. Row spacing 914 may be measured from the center 916 of a given row to the center 916 of an adjacent row, for example. Row spacing 914 may be any suitable distance for the crop. For example, row spacings used in some embodiments of the present invention might include 20, 22, 30, 36, 38, and 40 inch row spacings in order to be compatible with certain existing commercially available planting, tilling and/or harvesting equipment, although the exact spacing and/or units of measurement can be varied from the examples without departing from the scope of the invention as claimed.

Typically, the farm implement apparatus 950 is towed behind a tractor (not shown). The farm implement apparatus 950 is typically connected to the tractor with a draw-bar 952 as illustrated in FIG. 9, or a three-point hitch. In the embodiment illustrated in FIG. 9, the draw-bar 952 is attached to a header bar 954, which is attached to eight in-crop-row bars 956 and seven between-crop-row bars 958. The configuration of the farm implement apparatus 950 illustrated in FIG. 9 is an exemplary. One skilled in the art will appreciate that farm implement apparatus having other configurations are possible within the scope of the invention as claimed. For example, the size of the farm implement apparatus need not be 8-rows as illustrated in FIG. 9.

The farm implement apparatus 950 may be, for example, a modified-version of a conventional planter. An example of a suitable conventional planter is the John Deere MaxEmerge XP Planter, available from Deere and Company, Moline, Ill.

Conventional planters precisely sow seed along a number of rows, and typically vary in size from 2-rows to 48-rows. Seeds are distributed by conventional planters through devices referred to as "row units," which are spaced evenly across the planter. The space between the row units (typically referred to a "row spacing") can vary greatly, but typically the row spacing is 30 inches. Conventional planters typically have a seed bin for each row, as well as a fertilizer bin for each row. In each seed bin, plates are installed having a configuration (e.g., number of teeth and tooth spacing) based on the seed type and the sowing rate. The size of the space between the teeth is just large enough to accommodate one seed at a time. Other conventional planters have a large seed bin for seeds that are distributed to each row, in lieu of a seed bin for each row.

The farm implement apparatus 950 includes a seed bin 962 for each row, as well as a fertilizer bin 964 for each row. The seed bins 962 and the fertilizer bins 964, which are mounted on the in-crop-row bars 956, are conventional. A conventional "row unit" (not shown) underlies each of the seed bins 962. Similarly, a conventional dispersal device (not shown) underlies each of the fertilizer bins 964.

In accordance with some embodiments of the present invention, the farm implement apparatus 950 also includes one or more magnetic field generating devices (e.g., eight in-crop-row magnetic field generating devices 980 and seven between-crop-row magnetic field generating devices 985) and one or more herbicide bins (e.g., seven herbicide bins 995). The herbicide bins 995 are mounted on the between-crop-row bars 958. The in-crop-row magnetic field generating devices 980 are mounted on the in-crop-row bars 956, but the between-crop-row magnetic generating devices 985 are mounted on the between-crop-row bars 958. Each of the eight in-crop-row magnetic field generating devices 980 in FIG. 9 corresponds to the magnetic field generating device 205 in FIG. 2. Except with respect to their between-crop-row locations, the between-crop-row magnetic field generating devices 985 are substantially identical to the in-crop-row magnetic field generating devices 980. A conventional dispersal device (not shown) underlies each of the herbicide bins 995.

Preferably, the magnetic field generating devices 980 and 985 are configured to remain completely above ground. In an alternative embodiment, however, the magnetic field generating devices 980 and 985 may, at least partially, extend below ground (e.g., as probes). In another alternative embodiment, one or more of the magnetic field generating devices 980 and 985 may be stationary (e.g., mounted on poles or buried beneath the soil, especially in an environment such as a greenhouse) in lieu of, or in addition to, being mounted on the farm implement apparatus 950. In yet another alternative embodiment, one or more of the magnetic field generating devices 980 and 985 may be mounted on an aircraft in lieu of, or in addition to, being mounted on the farm implement apparatus 950.

In the embodiment illustrated in FIG. 9, the farm implement apparatus 950 is capable of performing several functions (described below) related to the use of microcapsules adapted to rupture in a magnetic field for controlled release of one or more agricultural chemicals. One skilled in the art will appreciate, however, that any number of these several functions may be performed individually or in subsets by separate farm implement apparatus or other apparatus without departing from the scope of the invention as claimed.

In some embodiments of the present invention, the farm implement apparatus 950 may be used in planting enhanced seeds (100 in FIGS. 1 and 2), as well as in subsequently triggering release of one or more agricultural chemicals from the microcapsules (125 in FIG. 1) coating the enhanced seed. For example, the enhanced seeds (i.e., seeds coated with microcapsules adapted to rupture in a magnetic field for controlled release of the one or more agricultural chemicals, such as a fertilizer) may be loaded into the seed bins 962 of the farm implement apparatus 950, which is then towed behind a tractor through a field to plant the enhanced seeds as the row crop 900. If the payload of the microcapsules coating the enhanced seeds is fertilizer, for example, the fertilizer bins 964 of the farm implement apparatus 950 need not be used. After the enhanced seeds have germinated and sprouted, the farm implement apparatus 950 is again towed behind a tractor through the field while the eight in-crop-row magnetic field generating devices 980 are activated to trigger release of the one or more agricultural chemicals (e.g., fertilizer) from the microcapsules coating the enhanced seed.

In other embodiments of the present invention, the farm implement apparatus 950 may be used in planting conventional seeds (301 in FIG. 3) while simultaneously applying microcapsules (325 in FIG. 3) adapted to rupture in a magnetic field for controlled release of one or more agricultural chemicals, as well as in subsequently triggering release of the one or more agricultural chemicals from the microcapsules.

In a first example, the conventional seeds may be loaded into the seed bins 962 and the microcapsules adapted to rupture in a magnetic field for controlled release of the one or more agricultural chemicals (e.g., a fertilizer) are loaded into the fertilizer bins 964 of the farm implement apparatus 950, which is then towed behind a tractor through a field to plant the seeds as the row crop 900 while simultaneously applying the microcapsules. After a suitable period of time has passed (e.g., after the conventional seeds have germinated and sprouted), the farm implement apparatus 950 is again towed behind a tractor through the field while the eight in-crop-row magnetic field generating devices 980 are activated to trigger release of the one or more agricultural chemicals from the microcapsules.

In a second example, the conventional seeds may be loaded into the seed bins 962 and the microcapsules adapted to rupture in a magnetic field for controlled release of the one or more agricultural chemicals (e.g., a phenoxy herbicide such as 2,4-Dichlorophenoxyacetic acid (2,4-D)) are loaded into the herbicide bins 995 of the farm implement apparatus 950, which is then towed behind a tractor through a field to plant the seeds as the row crop 900 while simultaneously applying the microcapsules in area 918 between the rows 912 of crop 900. After a suitable period of time has passed (e.g., after the conventional seeds have germinated and sprouted), the farm implement apparatus 950 is again towed behind a tractor through the field while the seven between-crop-row magnetic field generating devices 985 are activated to trigger "precision" release of the one or more agricultural chemicals from the microcapsules in area 918 between the rows 912 of crop 900. That is, the boundary of release is precisely controlled to be within area 918 between the rows 912 of crop 900 (and, importantly, not in the rows 912 of crop 900 to mitigate drift-area crop damage).

As mentioned above, 2,4-D is the most widely used herbicide in the world. When it was commercially released in 1946, 2,4-D became the first successful selective herbicide. It only kills broadleaf plants (also known as "dicots"), leaving behind grasses (also known as "monocots"). Hence, 2,4-D provides effective weed control in wheat, maize (corn), rice, and similar grass crops. Unfortunately, 2,4-D and other phenoxy herbicides can cause unwanted damage to certain crops located in drift areas (e.g., a crop row adjacent to where the herbicide is applied). Soybeans, potatoes, and other vegetable crops are particularly susceptible to such damage. As a consequence, some crops that have been genetically engineered to be resistant to 2,4-D. For example, genetically engineered maize (corn) and soybean resistance to 2,4-D has been demonstrated through insertion of a bacterial aryloxyalkanoate dioxygenase gene. Some embodiments of the present invention (e.g., the second example, above, and the yet other embodiments, below) provide an effective alternative to the use of such genetically engineered crops because the herbicide is precisely applied and easily triggered for "precision" release.

In yet other embodiments of the present invention, the farm implement apparatus 950 may be used in precisely triggering release of one or more agricultural chemicals (e.g., a phenoxy herbicide such as 2,4-Dichlorophenoxyacetic acid (2,4-D)) from microcapsules that were earlier broadly applied (e.g., sprayed via a conventional boom sprayer or aircraft) to the row crop 900. After the microcapsules have been broadly applied to the row crop 900, the farm implement apparatus 950 is towed behind a tractor through the field while the seven between-crop-row magnetic field generating devices 985 are activated to trigger "precision" release of the one or more agricultural chemicals from the microcapsules in area 918 between the rows 912 of crop 900. That is, the boundary of release is precisely controlled to be within area 918 between the rows 912 of crop 900 (and, importantly, not in the rows 912 of crop 900). Because the herbicide is broadly applied and easily triggered for "precision" release, such embodiments of the present invention provide an effective alternative to the use of crops genetically engineered to be herbicide resistant.

The precision release feature of some of the embodiments of the present invention provides a number of additional advantages. For example, the precision release feature makes it possible to broadly apply agricultural chemicals but yet mitigate the adverse effect of "drift" onto adjacent fields and other areas of inadvertent application. Also, the precision release feature makes it possible for farmers to use herbicides such as glyphosate (N-(phosphonomethyl)glycine) as a post-emergence herbicide without utilizing crops that have been genetically engineered to be resistant to such herbicides. Conventionally, the use of glyphosate as a post-emergence herbicide requires the use of such genetically engineered crops. As mentioned above, glyphosate is the most widely used herbicide in the United States. Glyphosate, which is commercially available under the tradename Roundup from Monsanto Company, St. Louis, Mo., is a broad-spectrum systemic herbicide used to kill weeds and grasses which commonly compete with crops. Because glyphosate is only effective on actively growing plants, it is not effective as a pre-emergence herbicide. Crops that have been genetically engineered to be resistant to glyphosate, for example, are available under the tradename Roundup Ready from Monsanto Company, St. Louis, Mo. Conventionally, such genetically engineered crops are required in order to use glyphosate as a post-emergence herbicide.

One skilled in the art will appreciate that many variations are possible within the scope of the present invention. For example, although some embodiments of the present invention are described herein in the context of producing and using formulations for controlled release of agricultural chemicals in row crops, the present invention may be utilized in the context of producing and using formulations for controlled release of one or more agricultural chemicals in other plants and environments such as greenhouse plants, house plants, trees, shrubs, bushes, grasses, weeds, flowers, and the like. Thus, while the present invention has been particularly shown and described with reference to some embodiments thereof, it will be understood by those skilled in the art that these and other changes in form and detail may be made therein without departing from the spirit and scope of the present invention.

What is claimed is:

1. A method of triggering controlled release of one or more agricultural chemicals from microcapsules adapted to rupture in a magnetic field and applied to at least one of soil, seeds and plants, wherein each microcapsule has a shell encapsulating an agricultural chemical and into which one or more organo trialkoxysilane-coated magnetic nanoparticles is/are covalently bound, and wherein the agricultural chemical is selected from a group of active ingredients consisting of fertilizers, herbicides, insecticides, and combinations thereof, the method comprising the steps of:

positioning a magnetic field generating device proximate the microcapsules;

activating the magnetic field generating device to generate a magnetic field sufficient to rupture the shell of the microcapsules through magnetic stimulation of the organo trialkoxysilane-coated magnetic nanoparticles, thereby releasing the agricultural chemical from the ruptured shell and into the application zone, wherein the agricultural chemical includes at least one fertilizer, wherein the microcapsules are applied during seed planting, and wherein the activating step is performed subsequent to seed planting.

2. A method of triggering controlled release of one or more agricultural chemicals from microcapsules adapted to rupture in a magnetic field and applied to at least one of soil, seeds and plants, wherein each microcapsule has a shell encapsulating an agricultural chemical and into which one or more organo trialkoxysilane-coated magnetic nanoparticles is/are covalently bound, and wherein the agricultural chemical is selected from a group of active ingredients consisting of fertilizers, herbicides, insecticides, and combinations thereof, the method comprising the steps of:

positioning a magnetic field generating device proximate the microcapsules;

activating the magnetic field generating device to generate a magnetic field sufficient to rupture the shell of the microcapsules through magnetic stimulation of the organo trialkoxysilane-coated magnetic nanoparticles, thereby releasing the agricultural chemical from the ruptured shell and into the application zone, wherein the agricultural chemical includes at least one herbicide and/or insecticide, wherein the microcapsules are selectively applied between adjacent rows of seed during seed planting, and wherein the activating step is selectively performed subsequent to seed planting.

3. A method of triggering controlled release of one or more agricultural chemicals from microcapsules adapted to rupture in a magnetic field and applied to at least one of soil, seeds and plants, wherein each microcapsule has a shell encapsulating an agricultural chemical and into which one or more organo trialkoxysilane-coated magnetic nanoparticles is/are covalently bound, and wherein the agricultural chemical is selected from a group of active ingredients consisting of fertilizers, herbicides, insecticides, and combinations thereof, the method comprising the steps of:

positioning a magnetic field generating device proximate the microcapsules;

activating the magnetic field generating device to generate a magnetic field sufficient to rupture the shell of the microcapsules through magnetic stimulation of the organo trialkoxysilane-coated magnetic nanoparticles, thereby releasing the agricultural chemical from the ruptured shell and into the application zone, wherein the agricultural chemical includes at least one herbicide and/or insecticide, wherein the microcapsules are broadly applied between adjacent rows of seed and in rows of seeds, and wherein the activating step is selectively performed between adjacent rows of seed.

* * * * *